United States Patent [19]

Cloyd

[11] 4,222,745

[45] Sep. 16, 1980

[54] INDICATOR FOR DETECTION OF $SO_2$ LEAKAGE

[75] Inventor: James S. Cloyd, Dayton, Ohio

[73] Assignee: The United States of America as represented by the Secretary of the Air Force, Washington, D.C.

[21] Appl. No.: 958,929

[22] Filed: Nov. 8, 1978

[51] Int. Cl.$^2$ ..................... G01N 21/06; G01N 21/12
[52] U.S. Cl. ................................. 23/230 L; 23/230 R; 23/232 R; 252/408; 429/90; 116/206
[58] Field of Search ......... 252/408; 23/230 L, 230 R, 23/232 R; 429/90

[56] References Cited

PUBLICATIONS

G. D. Patterson, Jr. et al., Anal. Chem., 24(10), 1586–1590 (Oct. 1952).

Primary Examiner—Sidney Marantz
Attorney, Agent, or Firm—Joseph E. Rusz; Vrftiv H. Kuhn

[57] ABSTRACT

A composition of matter comprising a mixture of (1) finely divided silica containing adsorbed potassium dichromate and (2) a polymeric adhesive material. The composition is particularly useful as an indicator for detecting the leakage of sulfur dioxide from cells and batteries.

6 Claims, No Drawings

INDICATOR FOR DETECTION OF SO₂ LEAKAGE

RIGHTS OF THE GOVERNMENT

The invention described herein may be manufactured and used by or for the Government of the United States for all governmental purposes without the payment of any royalty.

FIELD OF THE INVENTION

This invention relates to an indicator for detecting leakage of sulfur dioxide from cells and batteries. In one aspect, it relates to a method for detecting sulfur dioxide leakage from cells and batteries.

BACKGROUND OF THE INVENTION

Loss of sulfur dioxide from lithium-sulfur dioxide cells and batteries has been found to produce hazardous conditions. Thus, it has been proven that use of a defective Li-SO₂ cell or battery creates an explosive and possibly a shock-sensitive condition. Leakage from cells and batteries containing thionyl chloride (SOCl₂) and sulfuryl chloride (SO₂Cl₂) may also cause a dangerous situation as a result of chemical reaction with moisture to produce hydrochloric acid and sulfur dioxide.

Indicators have been previously used with certain systems to warn of exposure to adverse conditions such as electrolyte leakage and high temperature and humidity. For example, litmus paper has been utilized as a warning device for potassium hydroxide electrolyte leakage from nickel-cadmium batteries. In U.S. Pat. No. 2,785,959, there is disclosed a colorimetric method of determining the concentration of sulfur dioxide in a fluid medium in which siliceous gel granules impregnated with an ammonium or alkali metal vanadate is contacted with a sample of the medium.

It is an object of this invention to provide a composition of matter that is particularly adapted for detecting the leakage of sulfur dioxide from cells and batteries.

Another object of the invention is to provide a method for detecting the leakage of sulfur dioxide from cells and batteries.

Other objects and advantages of the invention will become apparent to those skilled in the art upon consideration of the accompanying disclosure.

SUMMARY OF THE INVENTION

The present invention resides in a composition comprising a mixture of (1) potassium dichromate adsorbed on finely divided silica and (2) a polymeric adhesive material. The amount of potassium dichromate (K₂Cr₂O₇) adsorbed on the silica generally ranges from about 3 to 5 parts by weight of K₂Cr₂O₇ per 100 parts by weight of silica. The amount of silica containing adsorbed K₂Cr₂O₇ usually ranges from about 20 to 60 parts by weight per 100 parts by weight of polymeric adhesive material. The composition has a paste-like consistency so that it can be readily applied to vertical as well as to horizontal surfaces.

In preparing the composition of this invention, the K₂Cr₂O₇ is added to distilled water while stirring to produce a yellow solution. The finely divided silica is then added to the yellow solution while continuing to stir for a sufficient length of time for the K₂Cr₂O₇ to be adsorbed on the silica. The stirring period can vary within rather broad limits, but a period of about 2 to 12 hours is usually sufficient to accomplish the desired adsorption. The amount of water used is only that which is sufficient to obtain a stirrable slurry. At the end of the stirring period, water is removed from the slurry so as to obtain silica containing adsorbed K₂Cr₂O₇. In a preferred procedure for removing the water, the slurry is poured into pans and the resulting sheets of material are allowed to dry at room temperature. It is also within the scope of the invention to heat the material, e.g., at a temperature ranging from 100° to 110° C., to expedite removal of the water or to separate the water by vacuum filtration. The dried silica containing adsorbed K₂Cr₂O₇ is collected and ground into a fine yellow powder. The K₂Cr₂O₇ adsorbed on silica is next thoroughly mixed with a polymeric adhesive material to form the composition of this invention.

To ensure the effectiveness of the composition as a sulfur dioxide indicator or warning system, it is usually preferred to employ an adhesive which is white or transluscent. Also, the adhesive is one that cures at room temperature upon exposure to atmospheric moisture. Examples of suitable adhesives include silicone rubbers which are well known polymers that can be obtained from commerical sources as white or transluscent, paste-consistency materials. It is often preferred to utilize polydimethylsiloxanes as the polymeric adhesive material. A silicone rubber that is particularly preferred is one having the following formula:

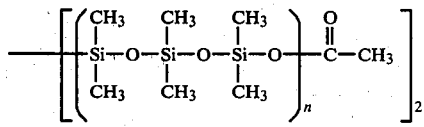

The subscript n is an integer having a value such that the molecular weight of the silicone rubber ranges from about 1000 to 4000. The silicone rubber has a paste-like consistency which cures to a tough, durable resilient rubber on exposure to atmospheric moisture at room temperature. The material cures through the acetoxy end groups, releasing small amounts of acetic acid vapors during the cure. To impart a white color to the silicone rubber, titanium dioxide filler in an amount ranging from about 25 to 75 weight percent can be mixed with the material. Silicone rubbers available from General Electric Company under product designations RTV 102 and RTV 112 can be used with advantage in the practice of the present invention.

In carrying out the method of this invention, the composition, prepared as described above, is spread, e.g., by means of a spatula, onto the battery or cell casing. The composition is usually spread on the casing at locations where leakage from the lithium-sulfur dioxide, lithium-thionyl chloride or lithium-sulfuryl chloride cells are most likely to occur, e.g., around or near the seals, weld points and vent mechanisms. Sulfur dioxide leaking from a cell or sulfur dioxide generated by leakage of precursor materials on contacting the composition changes its color from yellow to a bluish-green. By observing the composition and determining if a color change in the composition has occurred, it thus is possible to ascertain rapidly and conclusively whether hazardous battery conditions exist.

A more comprehensive understanding of the invention can be obtained by referring to the following illustrative examples which are not intended, however, to be unduly limitative of the invention.

EXAMPLE I

Potassium dichromate (0.50 g) was dissolved in 250 ml of distilled water. To this solution there was added 15.0 g of finely divided silica, a product of Cabot Corp. sold under the trademark Cab-O-Sil. The resulting slurry was stirred overnight during which time potassium dichromate was adsorbed by the silica. The thick yellow slurry obtained was poured into sheets and allowed to dry overnight. Thereafter, the material was collected and ground into a powder. A sample of this yellow powder changed to a dull blue-green color upon exposure to sulfur dioxide.

EXAMPLE II

A run was conducted in which 0.30 g finely divided silica containing adsorbed potassium dichromate, prepared as described in Example I, was dispersed by mixing in 1 g of a silicone rubber. The silicone rubber used, which was white in color, was a product of General Electric Company identified as RTV 102. The resulting mixture was yellow in color and had a paste-like consistency. The mixture was spreadable and when spread as a thin layer the silicone rubber cured through its acetoxy end groups. Upon exposure to sulfur dioxide, the yellow layer was transformed throughout to a blue-green color, indicating that the composition was sufficiently porous to allow the sulfur dioxide to permeate it and contact the adsorbed potassium dichromate. After storage for several weeks under ambient conditions, the composition remained blue-green in color, indicating that an irreversible color change had occurred.

From the foregoing, it is seen that the composition of this invention is an effective indicator for sulfur dioxide. Because of the nature of the composition, it can be readily applied to the casings of cells and batteries which may be subject to sulfur dioxide leakage or to leakage of precursors that generate sulfur dioxide. The composition thus makes it possible to provide an early warning of hazardous conditions that exist because of the presence of sulfur dioxide so that appropriate remedial action may be taken.

As will be evident to those skilled in the art, modifications of the present invention may be made in view of the foregoing disclosure without departing from the spirit and scope of the invention.

I claim:

1. A composition of matter having a paste-like consistency comprising a mixture of (1) potassium dichromate adsorbed on finely divided silica and (2) a silicone rubber.

2. The composition according to claim 1 in which the amount of potassium dichromate adsorbed on the silica ranges from about 3 to 5 parts by weight per 100 parts by weight of silica and the amount of silica containing adsorbed potassium dichromate ranges from about 20 to 60 parts by weight per 100 parts by weight of silicone rubber.

3. The composition according to claim 2 in which the silicone rubber is a polydimethylsiloxane.

4. The composition according to claim 2 in which the silicone rubber has the following formula:

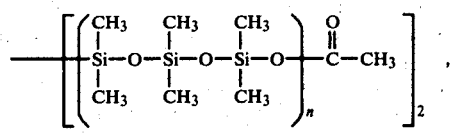

wherein n is an integer having a value such that the molecular weight of the silicone rubber ranges from about 1000 to 4000.

5. A method of detecting the leakage from lithium-sulfur dioxide, lithium thionyl chloride or lithium sulfuryl chloride cells of sulfur dioxide or sulfur dioxide generated by leakage of precursor materials, said method comprising the steps of applying to surfaces of the cells a composition yellow in color and having a paste-like consistency, said composition comprising a mixture of (1) potassium dichromate adsorbed on finely divided silica and (2) silicone rubber; and observing the composition so as to detect any color change therein, a change in color from yellow to bluish-green indicating leakage of sulfur dioxide or precursor materials.

6. The method of according to claim 5 in which the composition comprises about 3 to 5 parts by weight of potassium dichromate per 100 parts by weight of silica and about 20 to 60 parts by weight of silica containing adsorbed potassium dichromate per 100 parts by weight of silicone rubber.

* * * * *

UNITED STATES PATENT AND TRADEMARK OFFICE
CERTIFICATE OF CORRECTION

PATENT NO. : 4,222,745
DATED : September 16, 1980
INVENTOR(S) : James S. Cloyd

It is certified that error appears in the above-identified patent and that said Letters Patent are hereby corrected as shown below:

On the front sheet, change the given name of the second attorney from "Vrftiv" to -- Cedric --.

Signed and Sealed this

Seventeenth Day of February 1981

[SEAL]

Attest:

RENE D. TEGTMEYER

Attesting Officer     Acting Commissioner of Patents and Trademarks